US006430831B1

(12) United States Patent
Sundman

(10) Patent No.: US 6,430,831 B1
(45) Date of Patent: Aug. 13, 2002

(54) METHOD AND APPARATUS FOR MEASURING FOOT GEOMETRY

(75) Inventor: Arjen Sundman, Santa Cruz, CA (US)

(73) Assignee: Amfit, Inc., Santa Clara, CA (US)

( * ) Notice: Subject to any disclaimer, the term of this patent is extended or adjusted under 35 U.S.C. 154(b) by 82 days.

(21) Appl. No.: 09/705,106

(22) Filed: Nov. 2, 2000

Related U.S. Application Data
(60) Provisional application No. 60/164,090, filed on Nov. 6, 1999.

(51) Int. Cl.$^7$ ................................................ A61B 5/103
(52) U.S. Cl. ........................................ 33/515; 33/514.2
(58) Field of Search ............................... 33/515, 1 BB, 33/512, 514.2; 12/1 G, 21

(56) References Cited

U.S. PATENT DOCUMENTS

| 2,330,317 A | 9/1943 | Stewart ........................ 33/515 |
| 2,472,754 A | 6/1949 | Mead ........................... 33/515 |
| 4,998,354 A | 3/1991 | Silverman et al. ......... 33/514.2 |
| 5,390,680 A | 2/1995 | Brenner ....................... 33/515 |

*Primary Examiner*—Christopher W. Fulton
(74) *Attorney, Agent, or Firm*—Ohlandt, Greeley, Ruggiero & Perle, L.L.P.

(57) ABSTRACT

An apparatus for measuring a person's plantar contour having a foam impression block with a toe thickness and a heel thickness wherein the toe thickness is less than the heel thickness. A method for measuring a person's plantar contour using such a foam impression block by placing the plantar contour of the person's foot over the foam impression block such that the toes are over the toe thickness and the heel is over the heel thickness; and then pressing the plantar contour into the block to deform the block.

34 Claims, 12 Drawing Sheets

METHOD AND APPARATUS FOR MEASURING FOOT GEOMETRY

RELATED APPLICATION

This application claims priority of U.S. Provisional Application No. 60/164,090 filed on Nov. 6, 1999, the disclosure of which is incorporated herein by reference.

BACKGROUND OF THE INVENTION

1. Field of the Invention

The present invention relates to an apparatus and method of use for measuring the geometry of a foot. More particularly, the present invention further relates to an apparatus having a specially formed foam impression block. The present invention further relates to such an apparatus having a specially designed container. Moreover, the present invention further relates to methods of using such an apparatus for measuring the plantar contour and the instep of a foot.

2. Description of the Related Art

A number of methods currently exist to measure the geometry of a foot. These methods include plaster casting, optical scanning, contact sensor measurement, as well as foam impression measurement.

The optical scanning methods and contact sensor measurement methods utilize expensive equipment. These methods provide an accurate and complete measurement of the foot. But, the size, expense and complexity of the equipment necessary for these methods makes them not suitable for use in all locations.

Plaster casting methods require the measurement to be performed by a person other then the one being measured. This method provides an accurate and complete measurement of the foot but can be very messy and time consuming. Thus, plaster casting methods are not suitable for use in a person's home or by one's self.

Foam impression measurement methods and apparatus utilize an easily deformable foam block. A person steps onto the block, thus crushing the foam in the locations of higher pressure. In this manner, the foam block deforms in the approximate shape of the persons' plantar contour. The prior art produces a sub-optimal characterization of the foot for a number of reasons. First, the foam block is uniform in thickness from heel to toe. This causes the toes to be forced upward as the foot is pressed into the foam because the toes of the foot have substantially less pressure on them than the region of the foot from the heel to the metatarsal heads. Forcing the toes upward can cause a number of problems including, hyperextension of the plantar fascia, lowering of the correct arch height, and improper measurement of the forefoot and heel. Second, the prior art does not provide an accurate baseline for placement of the foot. Thus, it provides for a poor definition of the centerline of the foot that results in improper centering of the foot in the shoe. Next, the prior art a does not provide for measurement of the instep or of the upper forefoot. Moreover, placement of the foot in prior art impression blocks is not intuitive.

In the manufacture of custom insoles, the use of the plaster casting and foam impression methods described above also require the use of a scanning system. The scanning system in this instance, however, is centrally located at, for instance, a custom insole manufacturing facility. The scanning system may act directly on the negative impression within the foam or plaster. Scanning systems that act directly on negative impressions are known in the art. These laser-scanning systems consist of a laser with a line generating optic. The laser projects a line at a known incident angle onto the negative impression. A camera is used to read the position of the laser line on the negative impression. Alternatively, the scanning system may act on a positive plaster model made from the negative impression within the plaster or foam. Scanning systems that act directly on the positive impressions are also known in the art. One such scanning system, provided by U.S. Pat. No. 4,876,758, specially constructed array of pin-like sensors. In either circumstance, the scanning system is used to digitize the measured contour. The digitized contour is provided to a computer controlled milling machine. The milling machine uses the digitized information to manufacturing a custom insole matching the digitized contour. Accordingly, the apparatus and methods of the present invention provide for cheaper and easier means to provide custom manufactured insoles to a customer. Moreover, the present invention provides a foot measurement apparatus and method that overcome the limitations set forth above.

SUMMARY OF THE INVENTION

The present invention provides an apparatus for measuring a person's plantar contour and/or instep. The apparatus has a foam impression block with a toe thickness and a heel thickness; provided that the toe thickness is less than the heel thickness.

The apparatus also has a first holding case wherein the block is disposed. The case has an opening for accessing the block. The opening is shaped to approximate the shape of either a left foot or a right foot.

The apparatus also has a compliant medium with a plurality of straps having sizing graduations thereon. The compliant medium is placed on the block and acts to prevent the block from adhering to the user's foot. The straps are adapted to wrap around the foot and the graduations are used to indicate the height of the instep.

The present invention also provides a method for measuring a person's plantar contour. The method involves the steps of placing the plantar contour of the person's foot over a foam impression block with a toe thickness and a heel thickness; provided that the toe thickness is less than the heel thickness, and pressing the plantar contour into the block to deform the block.

Furthermore, the present invention provides a method for measuring a person's plantar contour. The method involves the steps of placing the plantar contour of the person's first foot over a foam impression block disposed within a first case; aligning the first foot such that the person's toes are over the toe thickness and the person's heel is over the heel thickness provided that the toe thickness is less than the heel thickness; and pressing the plantar contour through the opening into the block to deform the block.

Alternatively, the present invention acording to another embodiment includes a method involving the steps of placing the plantar contour of the person's first foot over a foam impression block disposed within a first case; aligning the first foot such that the person's toes are over the toe thickness and the person's heel is over the heel thickness provided that the toe thickness is less than the heel thickness; pressing the plantar contour through the opening onto the compliant medium and into the block to deform the block; wrapping at least one strap around the instep of the foot perpendicular to the length of the foot; and noting the perimeter indicated by the graduations on each strap.

DETAILED DESCRIPTION OF THE PREFERRED EMBODIMENT

Figure 1:
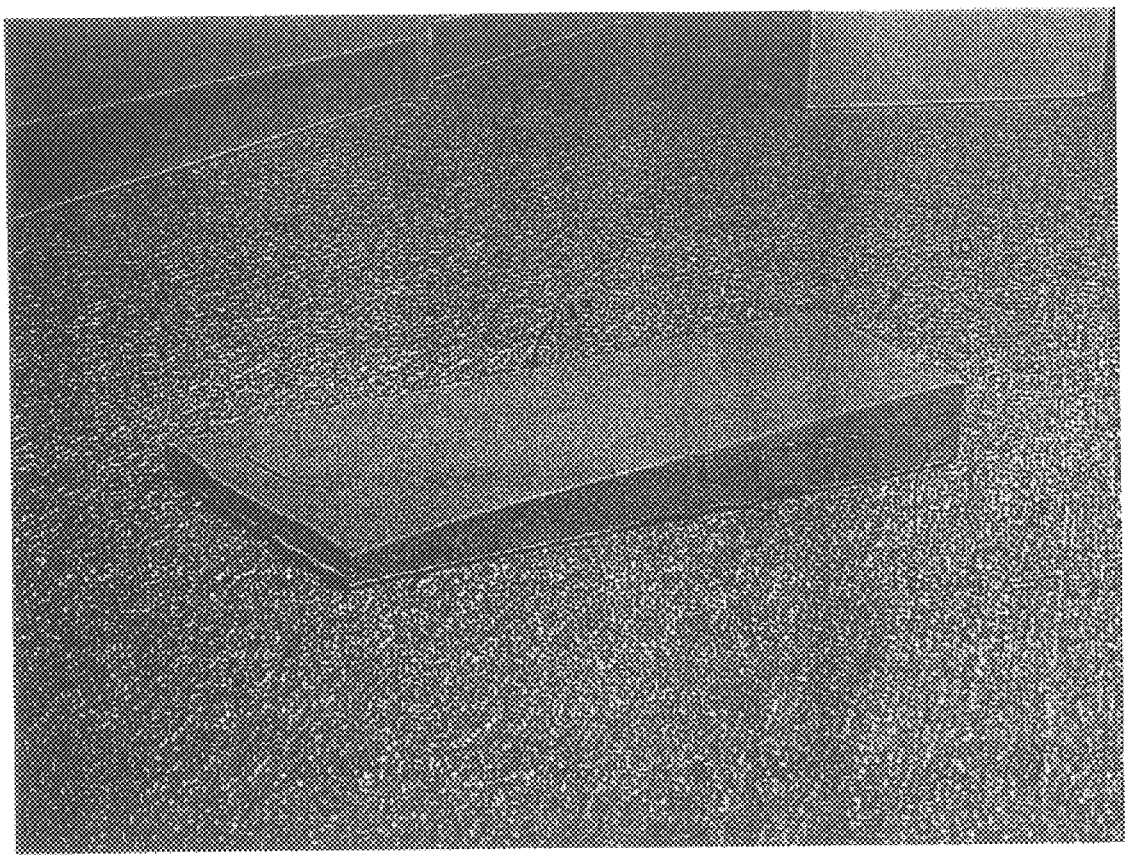
FIG. 1 is a perspective view of the foam block of the present invention.

Referring to the figures and more particularly to FIG. 1, a foam impression block is shown and is generally designated by the number 10. Block 10 is made from pressure sensitive materials that compress when a person's foot is pressed into the block. Preferably, block 10 comprises a foam casting material having low density, high flexural modulus and low shear strength. Accordingly, block 10 provides a material that is easily deformed, with little or no memory, and retains the deformed shape indefinitely. Expanded phenolic materials such as those commonly used for insulation and ultra low density expanded polystyrene are suitable for block 10. In the preferred embodiment, block 10 is expanded phenolic material.

Block 10 has a toe thickness 14, a heel thickness 18 and a length 19 that provide the block with a wedge-like shape. Toe thickness 14 is less than heel thickness 18, which minimizes any tendency for the toes of a person's foot to lift up while being pressed into block 10. For instance in a first embodiment, heel thickness 18 is in a range from about 20 mm to about 35 mm and toe thickness 14 is in a range from about 10 mm to about 15 mm. In the preferred embodiment, heel thickness 18 is approximately 35 mm and toe thickness 14 is approximately 10 mm. It should be recognized that any combination of toe thickness 14 being less than heel thickness 18, which minimizes the tendency for the toes of a person's foot to lift up while being pressed into block 10, are included within the scope of the present invention.

Figure 2:
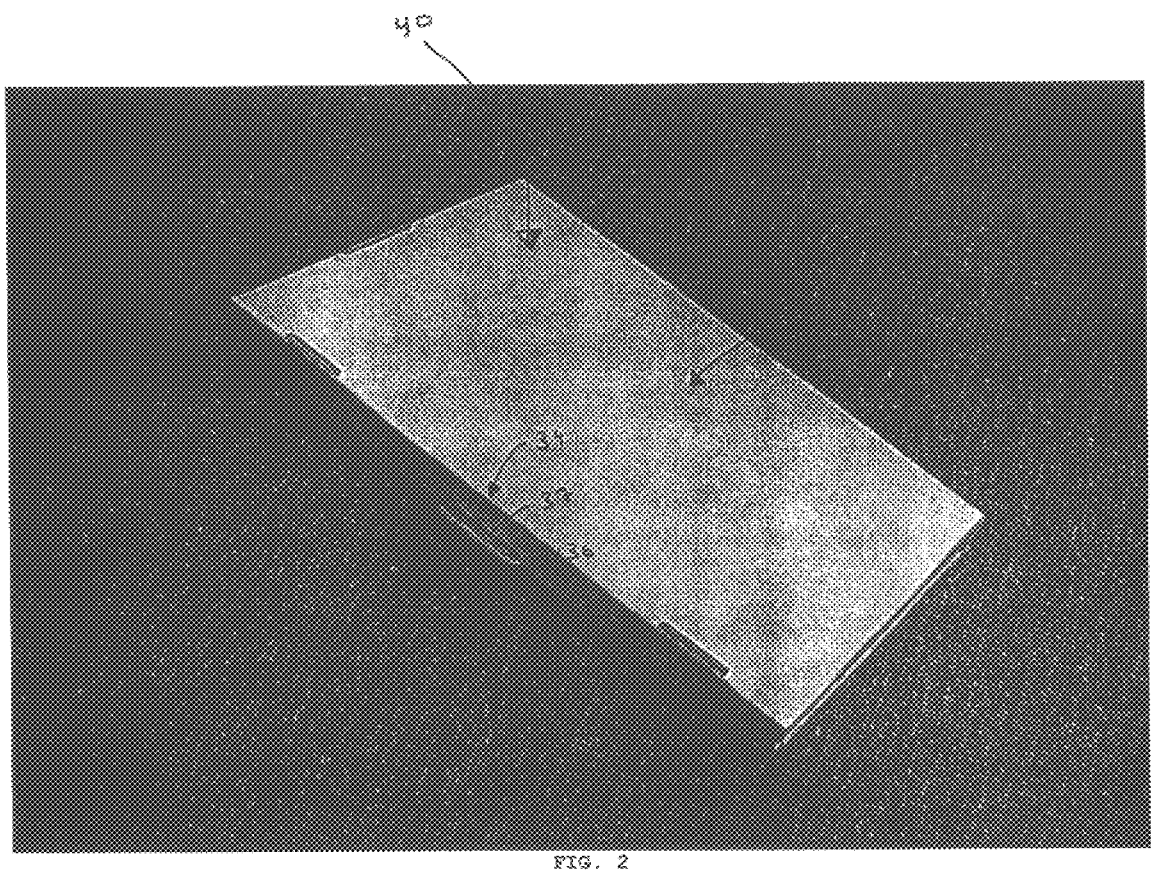
FIG. 2 is a perspective view showing the case for the foam block of FIG. 1 in a closed position.
Figure 3:
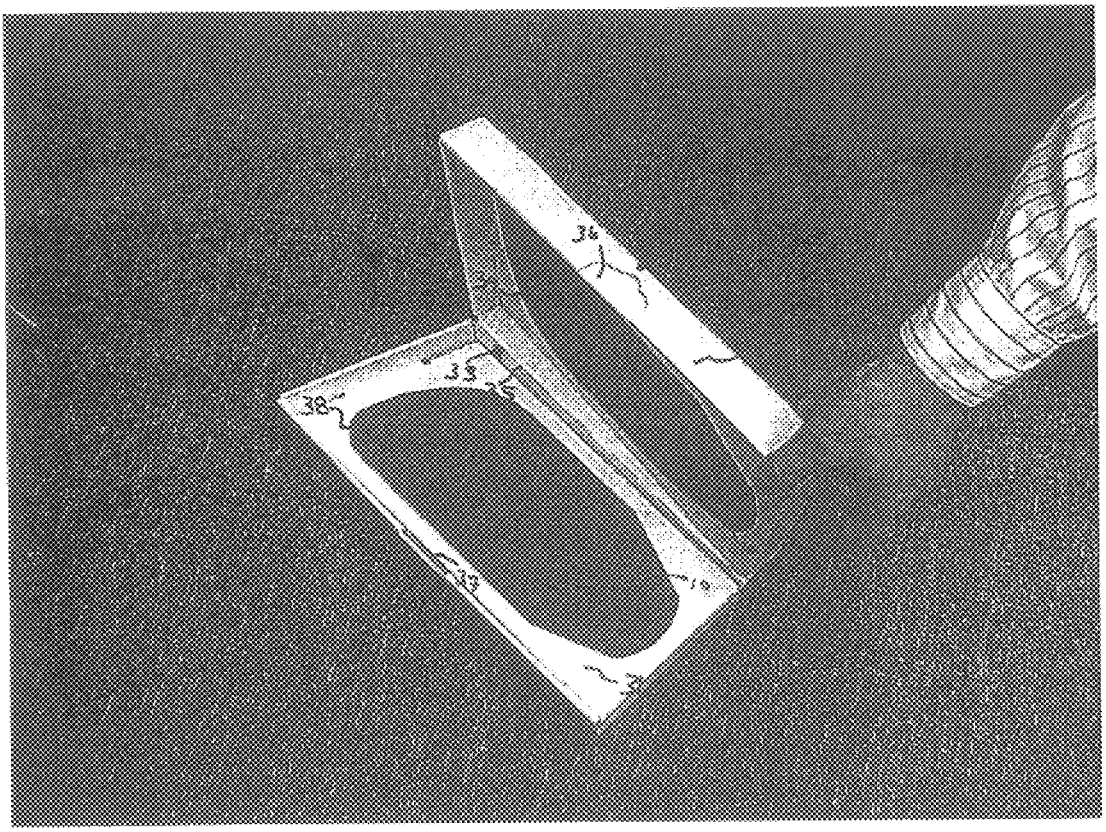
FIG. 3 is a perspective view showing the case in a partially open position.
Figure 4:
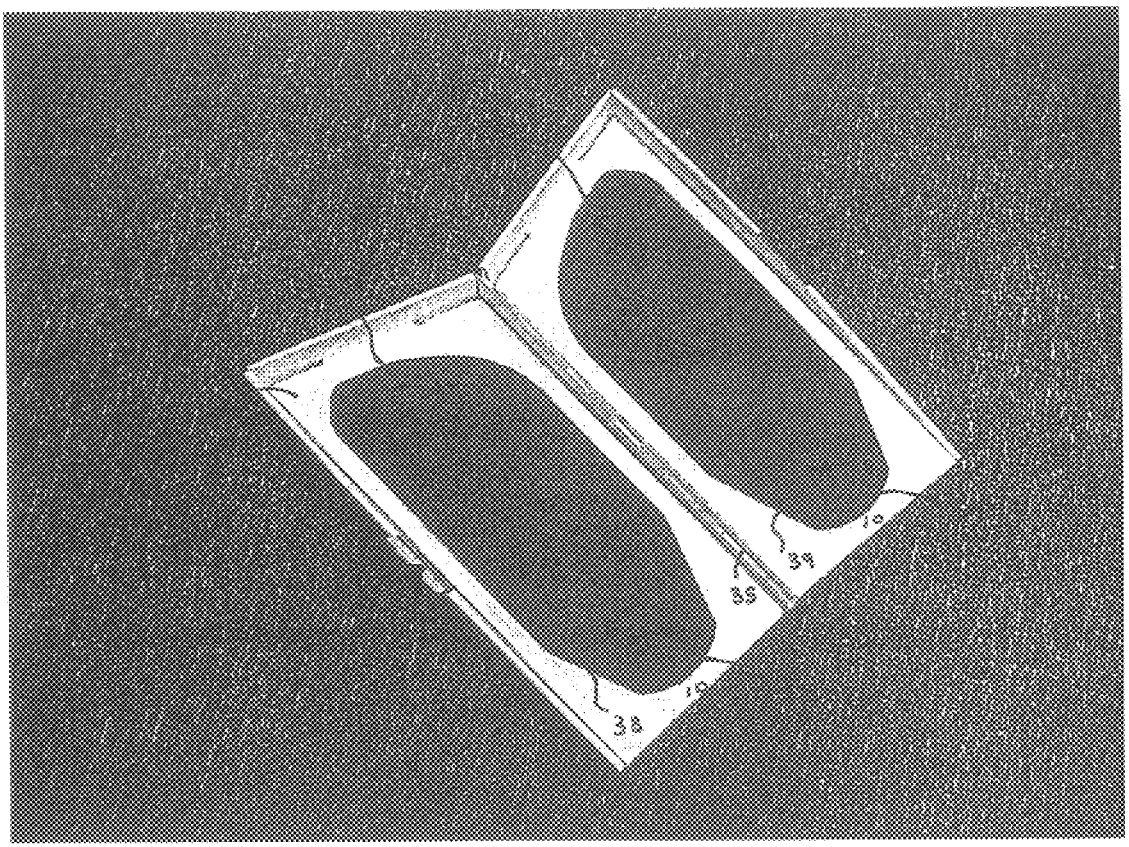
FIG. 4 is a perspective view showing the case in a completely open position.

Preferably, block 10 is provided with a case 30 as shown in FIGS. 2 through 4. Case 30 is used for storage, shipping, and protection of blocks 10 housed therein and as a guide for placing the foot in the blocks. Case 30 is made of inexpensive, lightweight materials suitable for shipping and storage such as, but not limited to, plastic or cardboard. In the preferred embodiment, case 30 is made of cardboard.

Case 30 has a first side 31, a second side 32, a hinge 33 and a clasp 34. First side 31 has one block 10 and second side 32 has another block 10 disposed therein. Side 31 has a right foot opening 38 shaped to approximate the shape of a right foot. Side 32 has a left foot opening 39 shaped to approximate the shape of a left foot. Openings 38, 39 provide access to blocks 10 within each side 31, 32, respectively.

Opening 38 has a heel portion 38-1 and a toe portion 38-2. Similarly, opening 39 has a heel portion 39-1 and a toe portion 39-2. Blocks 10 are positioned within sides 31, 32 such that toe thickness 14 is toward toe portion 38-1, 39-1 and heel thickness 18 is toward heel portion 38-2, 39-2, as shown in FIG. 4.

The foot-like shape of openings 38, 39 provides an intuitive indication of the proper positioning of the foot in blocks 10. Moreover, heel portions 38-2, 39-2 provide a guide for the user to place the heel of their foot. It should be noted that in a preferred embodiment, openings 38, 39 are placed within sides 31, 32 opposite where they occur on the body. Namely, right foot opening 38 is within side 31 that is to the left of left foot opening 39 within side 32. This ensures that the user only measures one foot at a time. If foot openings 38, 39 were positioned within sides 31, 32 such that the right foot opening was on the right side and the left foot opening was on the left side, the intuitive thing to do would be to place one foot in block 10 and then lift up the other foot and place it on the other block. This would render block 10 deformed by the first foot useless due to the unavoidable shifting of body weight as the second foot is lifted and placed into its block 10.

First side 31 is connected to second side 32 by hinge 33. Hinge 33 is provided to move case 30 between a closed position 40, shown in FIG. 2, and an open position 50, shown in FIG. 4. Clasp 34 is provided to releasably seal first side 31 and second side 32 in closed position 40. In closed position 40, blocks 10 are protected and hidden by case 30. In open position 50, blocks 10 are accessible via openings 38, 39, respectively.

In the preferred embodiment where case 30 comprises cardboard materials, hinge 33 is a perforated bend line 35 within the cardboard between first side 31 and second side 32 and clasp 34 comprises a tab 36 and a matching slot 37. Tab 36 is disposed on either side 31,32 with slot 37 positioned in a corresponding location of the other side 31,32, respectively. Slot 37 is adapted to receive tab 36, and the tab is adapted to engage the slot to releasably seal first side 31 and second side 32 in the closed position 40. Preferably, tab 36 and slot 37 utilizes a hook and loop type fastener to releasably seal first side 31 and second side 32 in the closed position 40.

Figure 5:
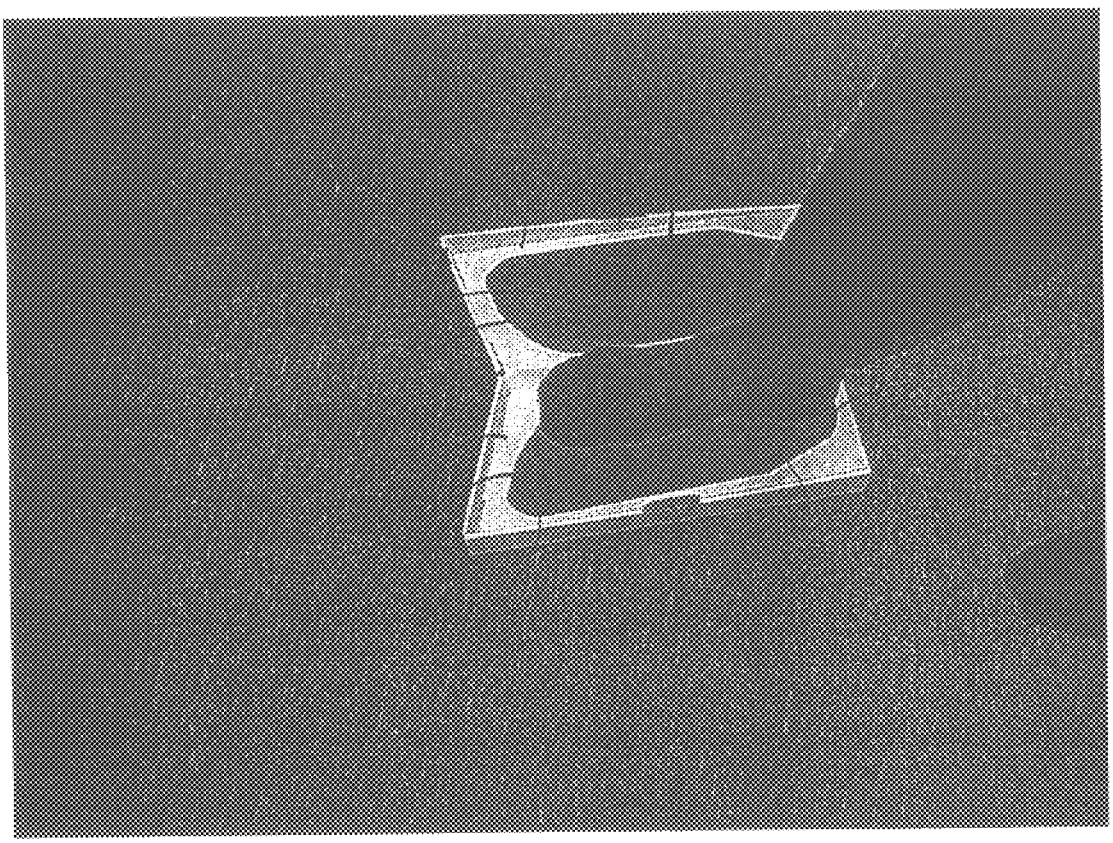
FIG. 5 is a perspective view of a foot being placed on the foam block.
Figure 6:
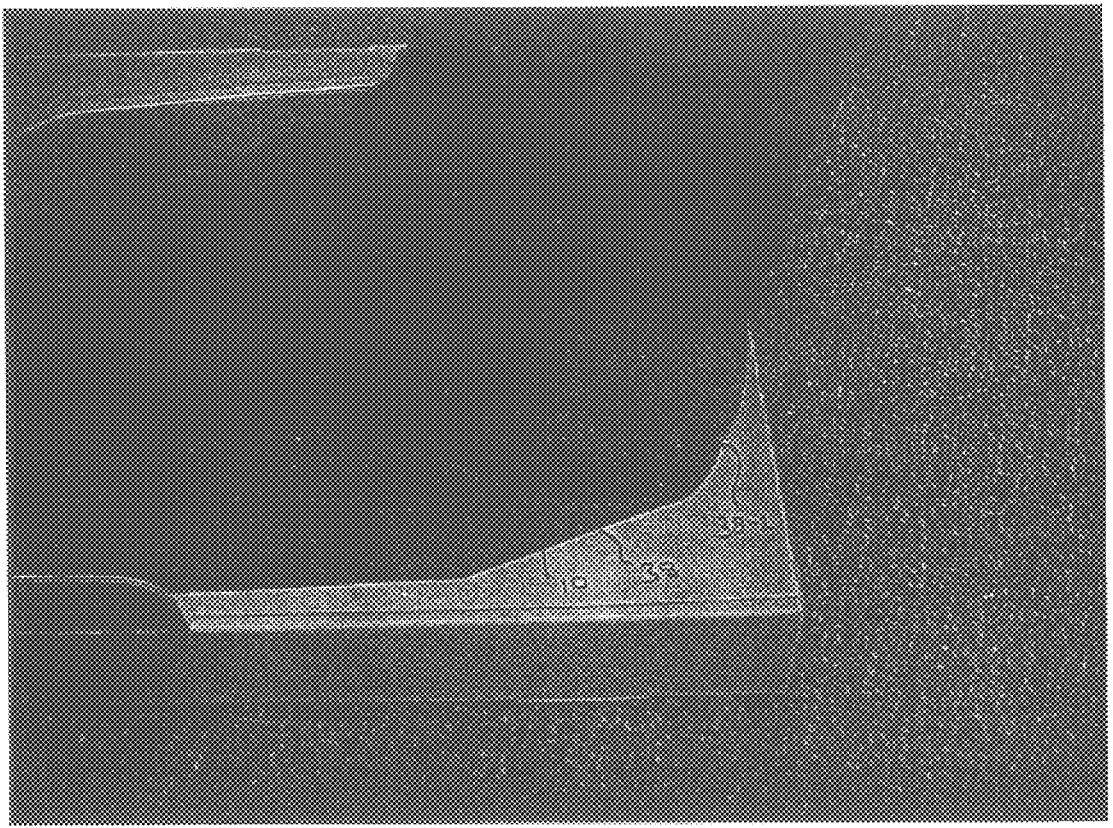
FIG. 6 is a perspective view of the heel of a foot being aligned with the heel portion of the case.
Figure 7:
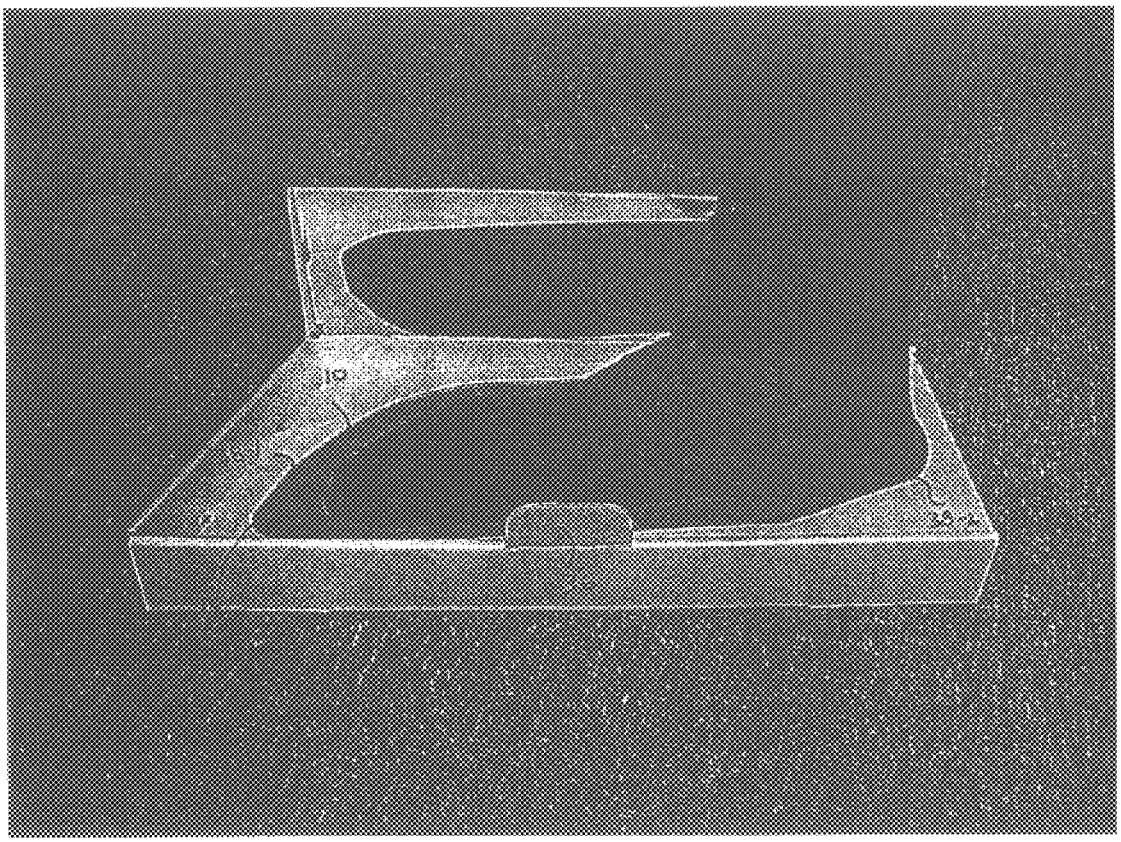
FIG. 7 is a perspective view of the foot fully deforming the foam block.
Figure 8:
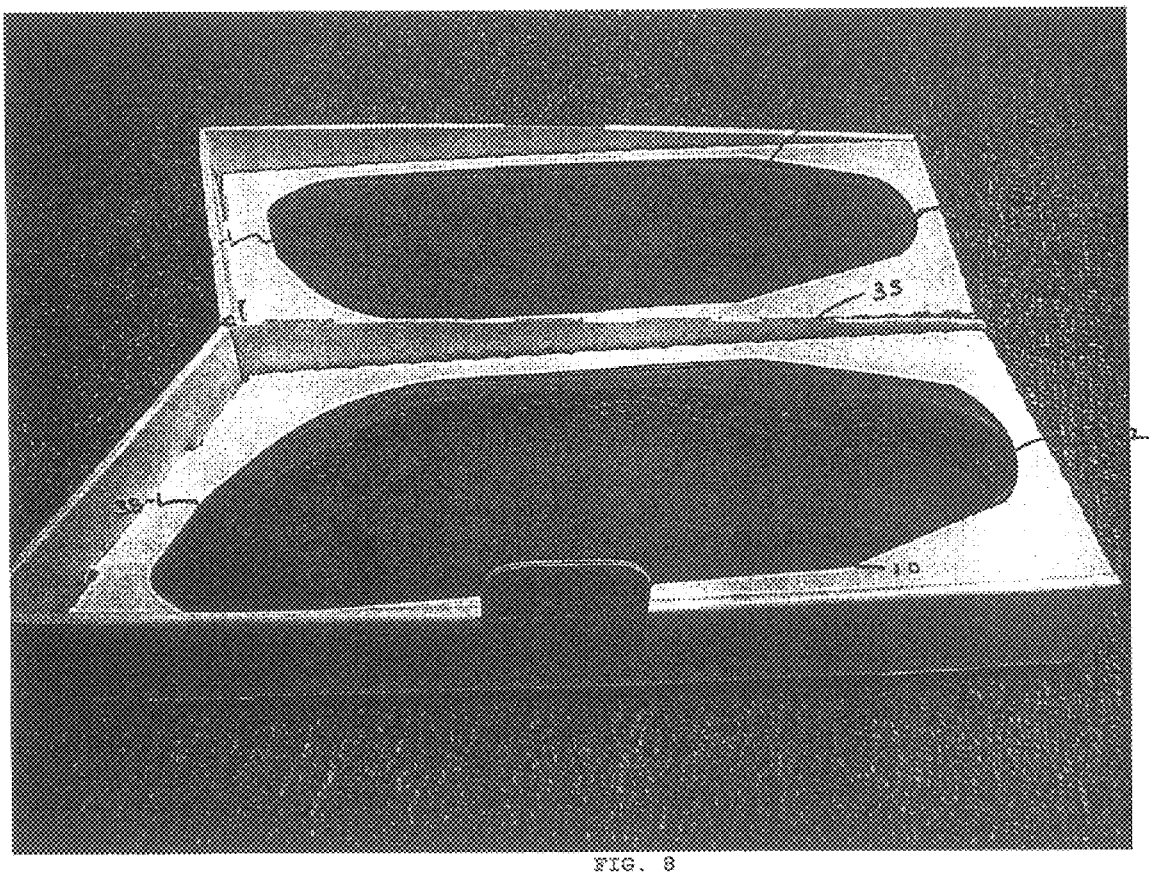
FIG. 8 is a perspective view of the deformed foam block after the foot has been removed.

In use to measure a person's plantar contour, the user moves case 30 into open position 50 and places the case on a flat surface, such as the floor. Next, the user places one foot into block 10 and applies weight to that foot until the block is fully deformed. Then, the user removes that foot and places the other foot into the other block 10 and applies weight to that foot until the block is fully deformed. More particularly, as shown in FIG. 5, the user places their right foot over block 10 of side 31 through opening 38. The user positions the heel of their right foot against the heel portion 38-2 of side 31, as shown in FIG. 6. The user then applies pressure to block 10 with their foot until the block is fully deformed, as shown in FIG. 7. When the user removes their foot from deformed block 10, the shaped and contour of their plantar contour is left within block 10, as shown in FIG. 8. The user then repeats these steps with their left foot. Upon completion of both feet, the user closes sides 31, 32 of case 30 via hinge 33 to fully closed position 40 and seals them via clasp 34.

In an alternate embodiment of the present invention, case 30 has been modified to provide for measurement of the instep or top surface of the foot. This information is also required to properly fit footwear. A person with a "high instep" would require a shoe that is deeper and may prevent the person from properly fitting into snugger fitting footwear. Further, by knowing the instep of a subject foot and knowing the internal geometry of a particular shoe, it is possible to determine if the shoe will fit properly. This information is vital when manufacturing custom plantar contours. For instance, if it is known via measurement using the present invention that there will be 2 mm of extra space in the shoe, it is possible to tailor the characteristics of the plantar contours to take up this extra space.

Figure 9:
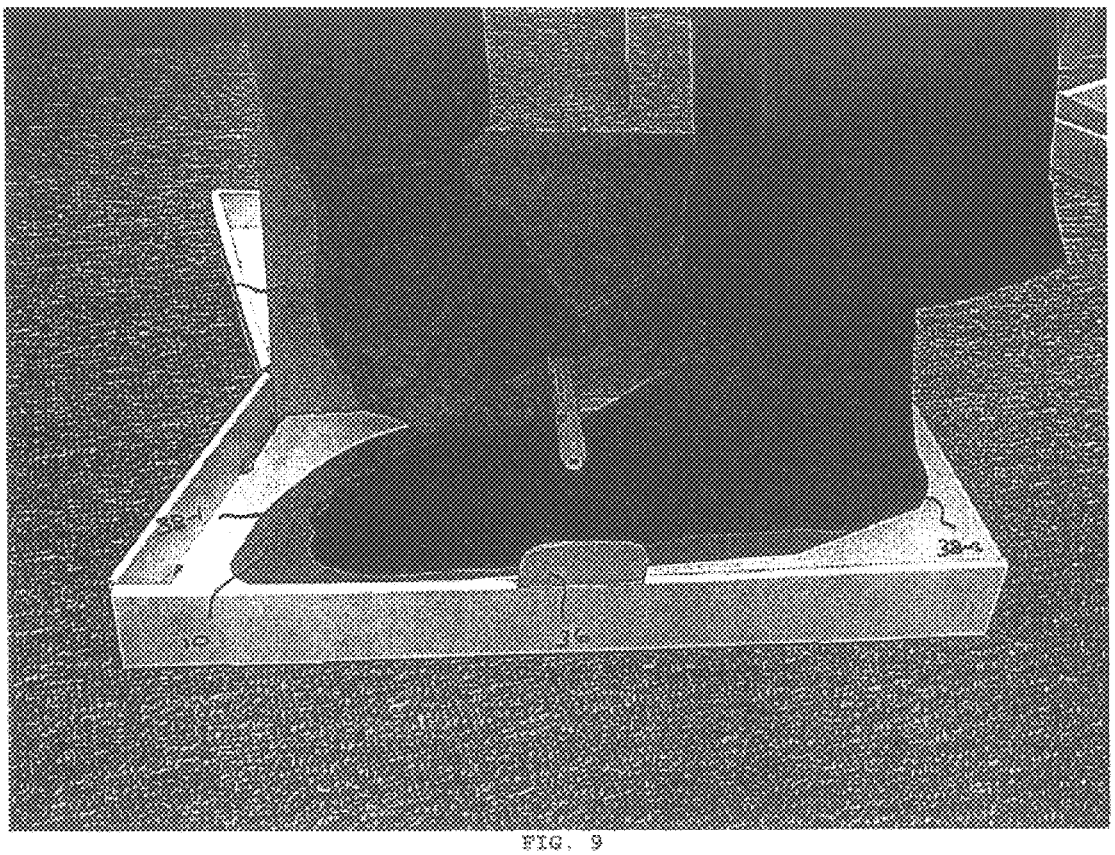
FIG. 9 is a perspective view of a first embodiment for measuring the instep of the foot.

A first modification to case 30 to measure the instep is shown in FIG. 9. In this embodiment, case 30 includes vertical portion 70. Once the person has fully deformed one of the blocks 10 with their foot, they use a pen 74 pressed against the top of their foot to trace the profile of their instep onto vertical portion 70 forming a trace line 72. Vertical portion 70 is adapted to removably fit between hinge 33 and sides 31 and 32.

Figure 10:
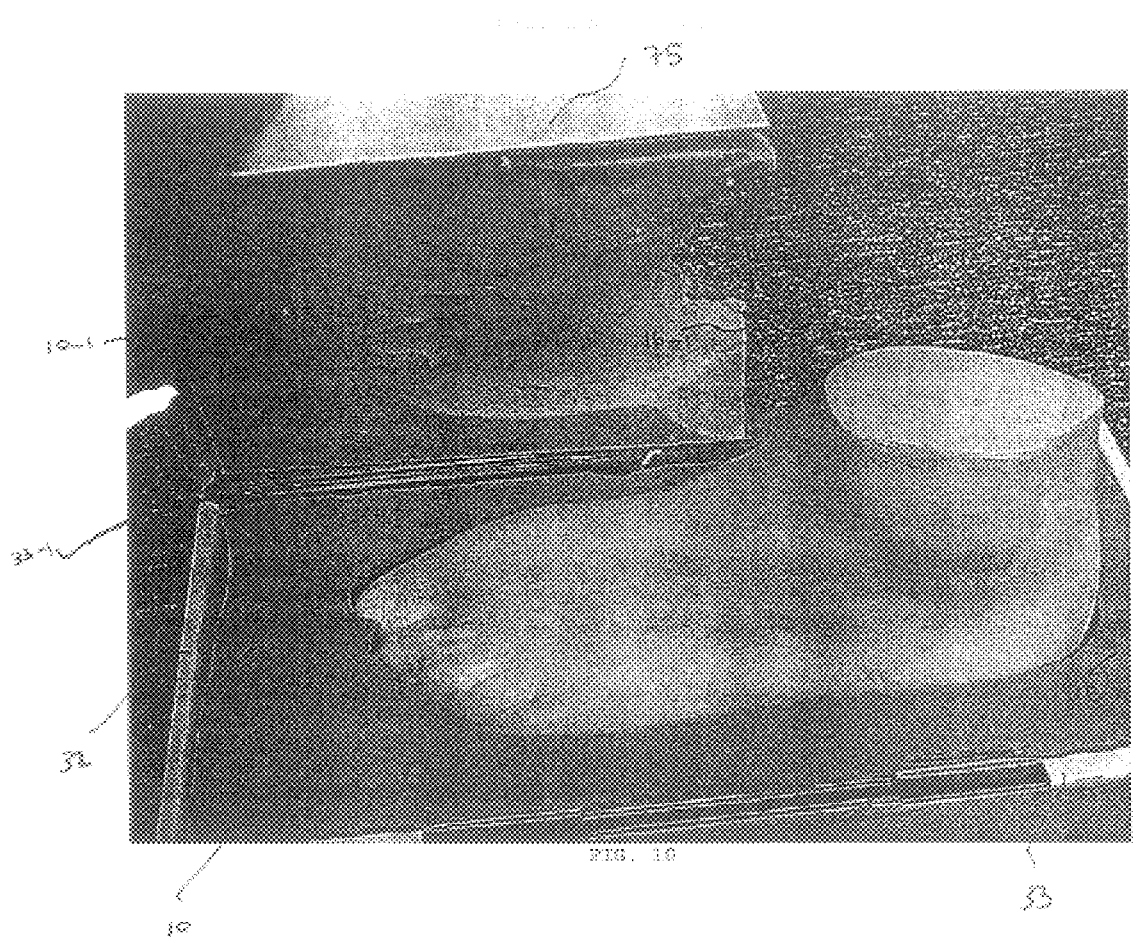
FIG. 10 is a perspective view of a second embodiment for measuring the instep of the foot.

A second modification to case 30 to measure the instep is shown in FIG. 10. In this embodiment, side 32 further includes a top section 75 connected by a second hinge 33-1 to the side opposite hinge 33. Top section 75 includes a partial block 10-1. Partial block 10 has a toe portion 14-1 and an ankle portion 16-1. Once the person has fully deformed block 10 within side 32, section 75 is moved via hinge 33-1 to contact block 10-1 against the top of the foot. It should be noted that while not shown in FIG. 10, it should be considered within the scope of the invention for case 30 to include a top section 75 for side 31 identical to top section 75 shown and described for side 32.

Figure 11:
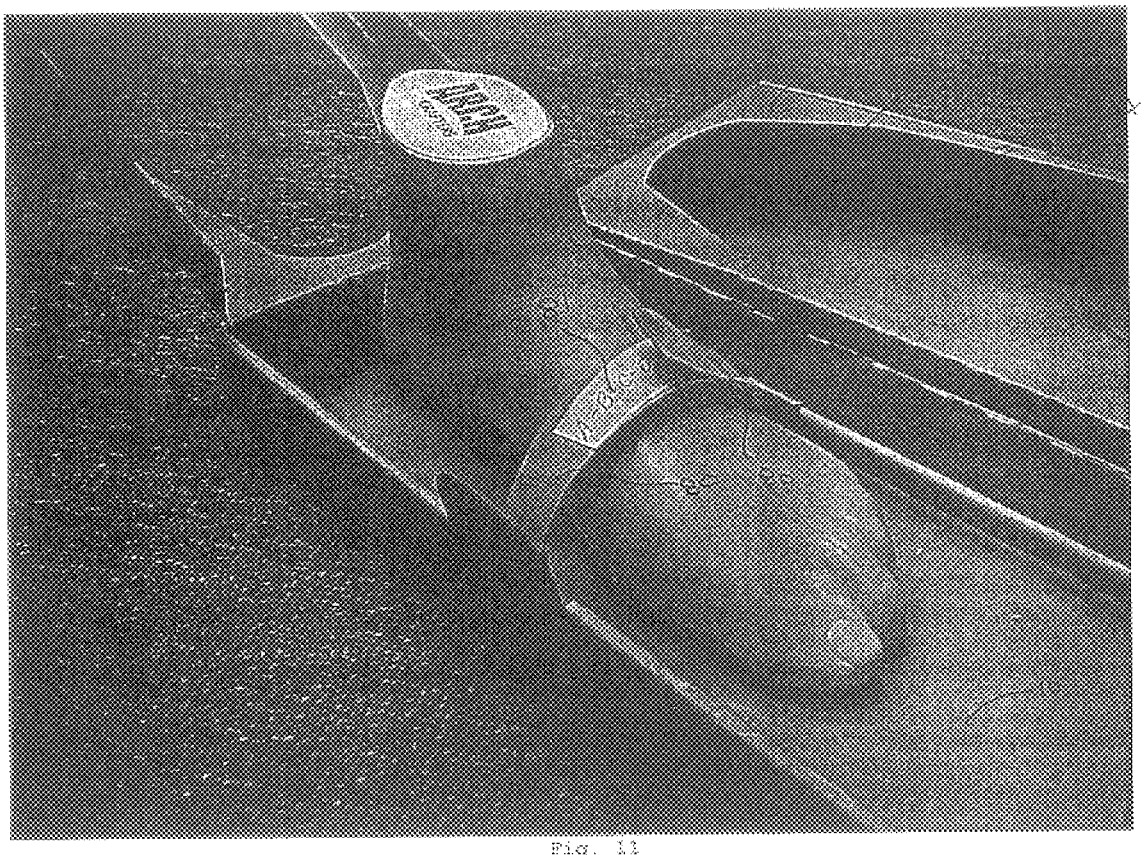
FIG. 11 is a perspective view of a third embodiment for measuring the instep of the foot.

In another embodiment, straps 80 are used to characterize the instep, as shown in FIG. 11. Straps 80 are coupled to case 30 and are adapted to be coupled over the instep of the user. Once coupled, graduations 81 on strap 80 indicate the height of the instep. Straps 80 are also adapted to slide within case 30 along the length of the users' foot. Thus, multiple measurements of the height of the instep can be taken along the length of the foot.

Figure 12:
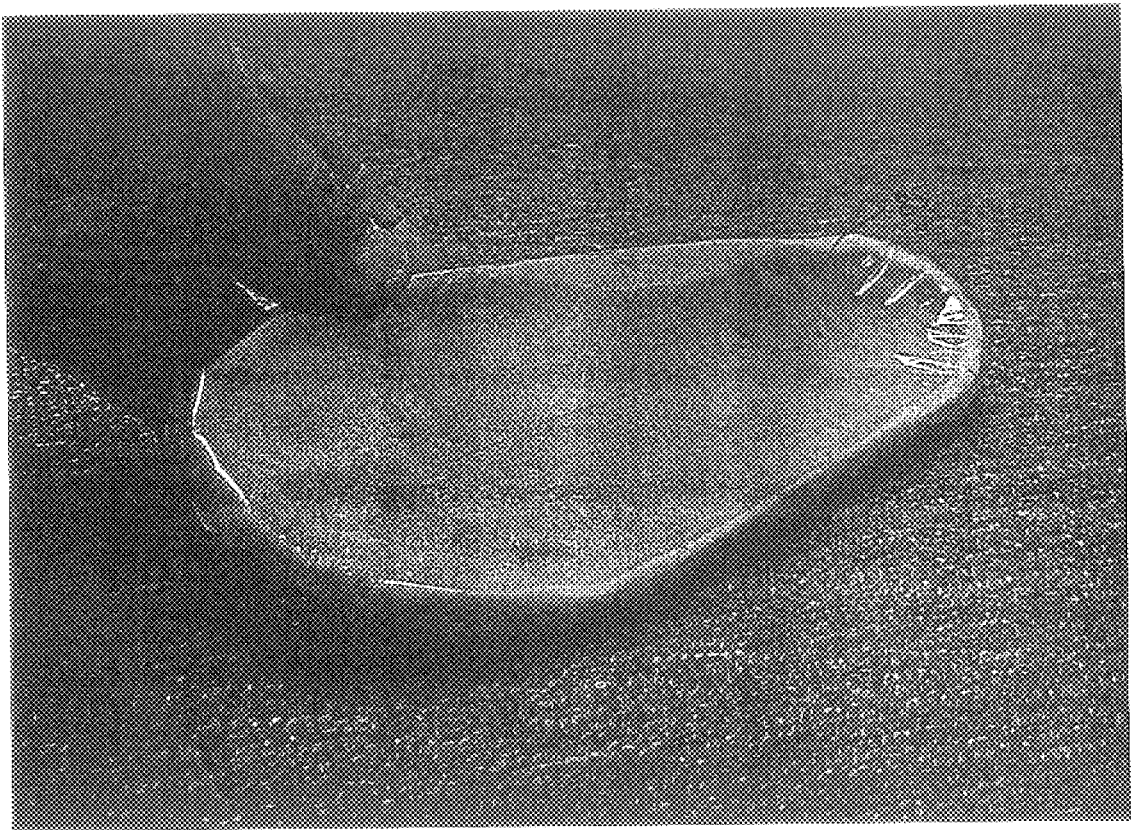
FIG. 12 is a perspective view of a fourth embodiment for measuring the instep of the foot.
Figure 1:
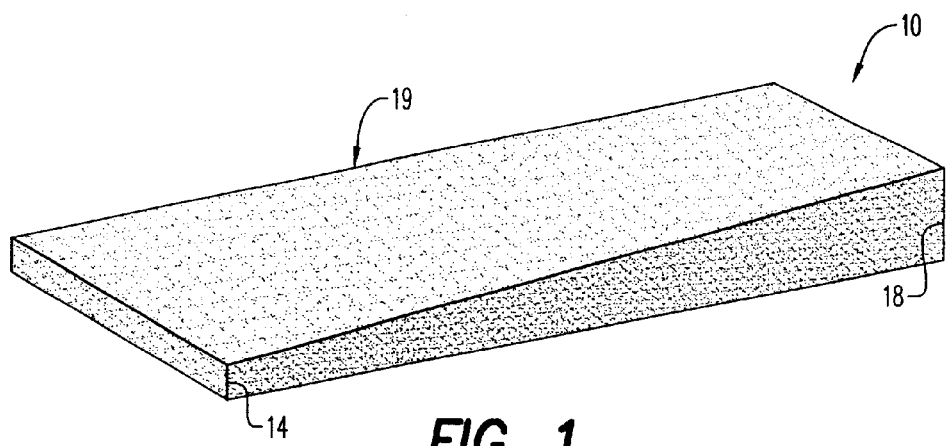
Figure 2:
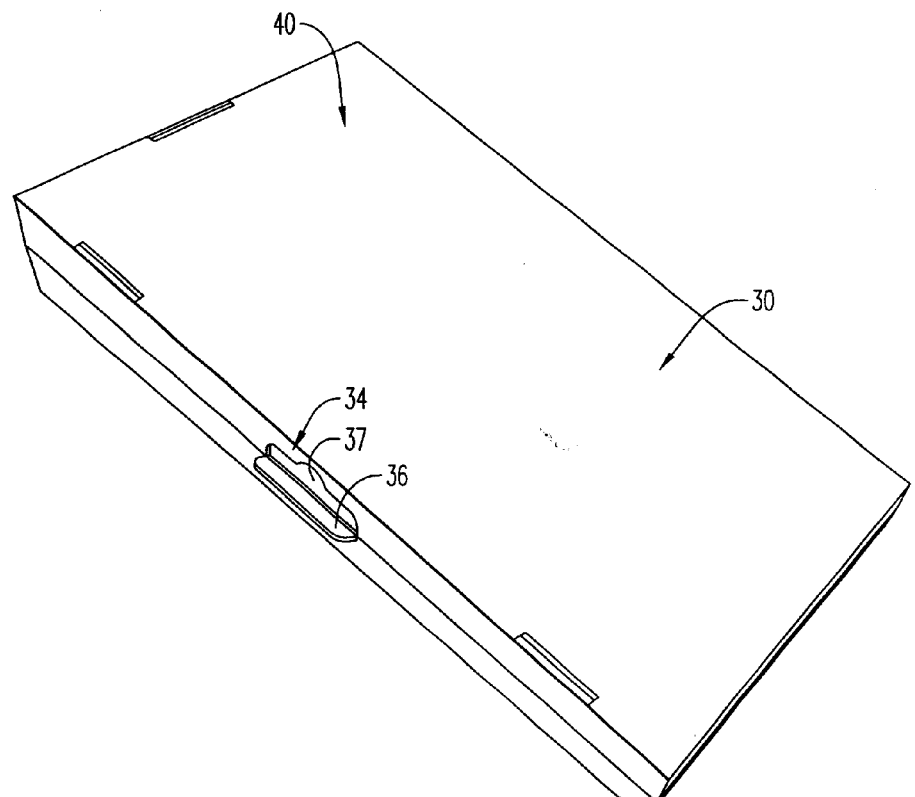
Figure 3:
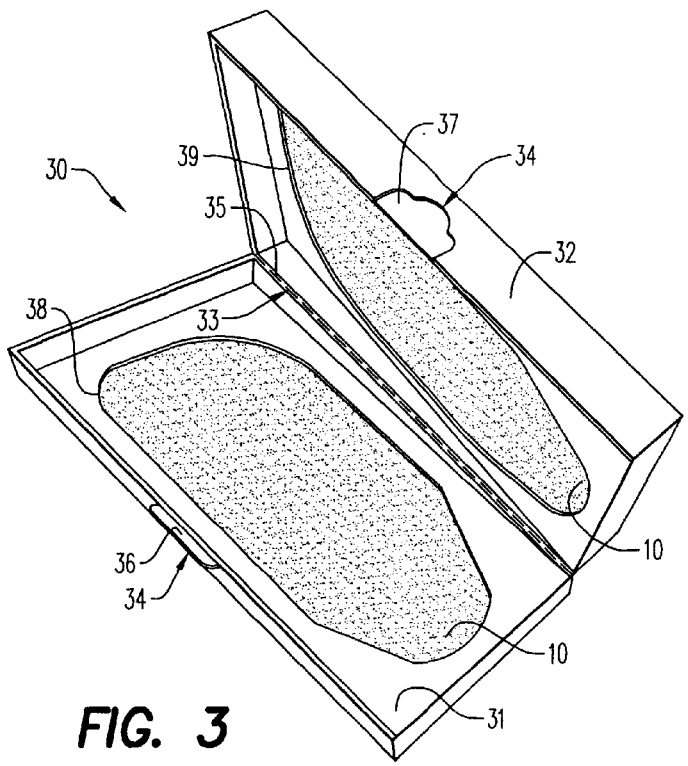
Figure 4:
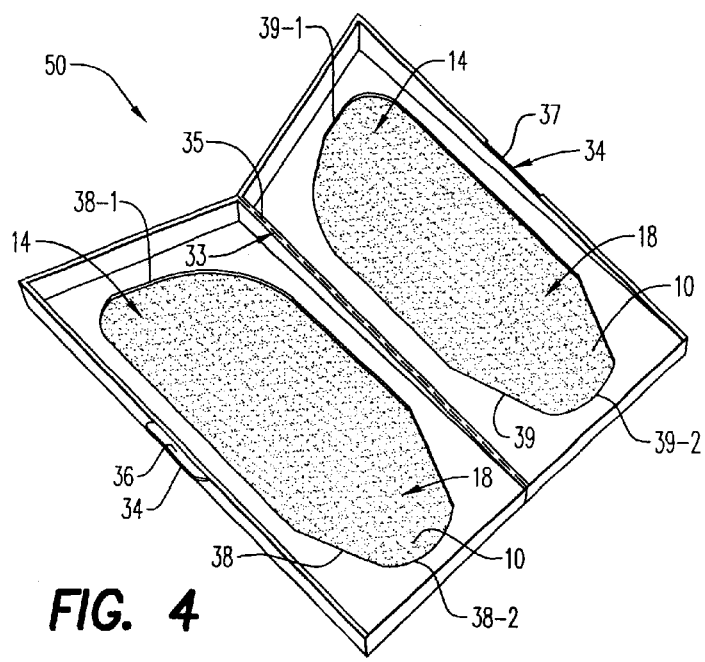
Figure 5:
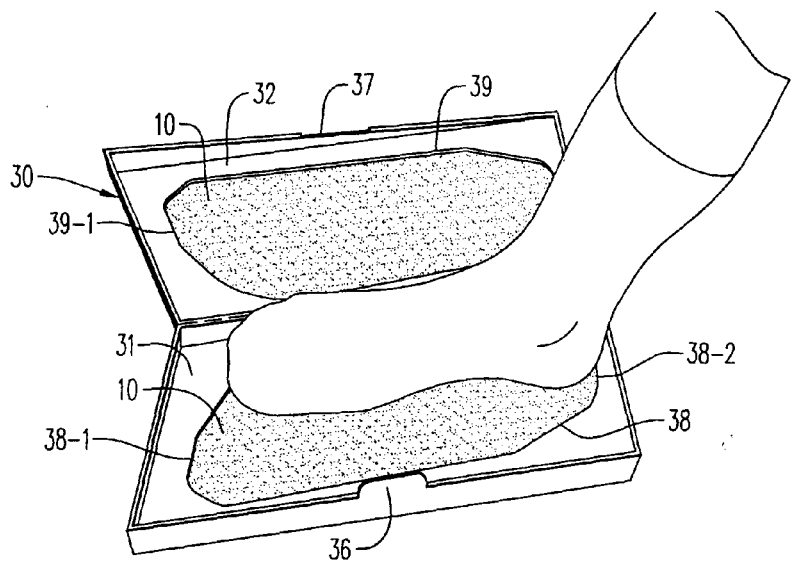
Figure 6:
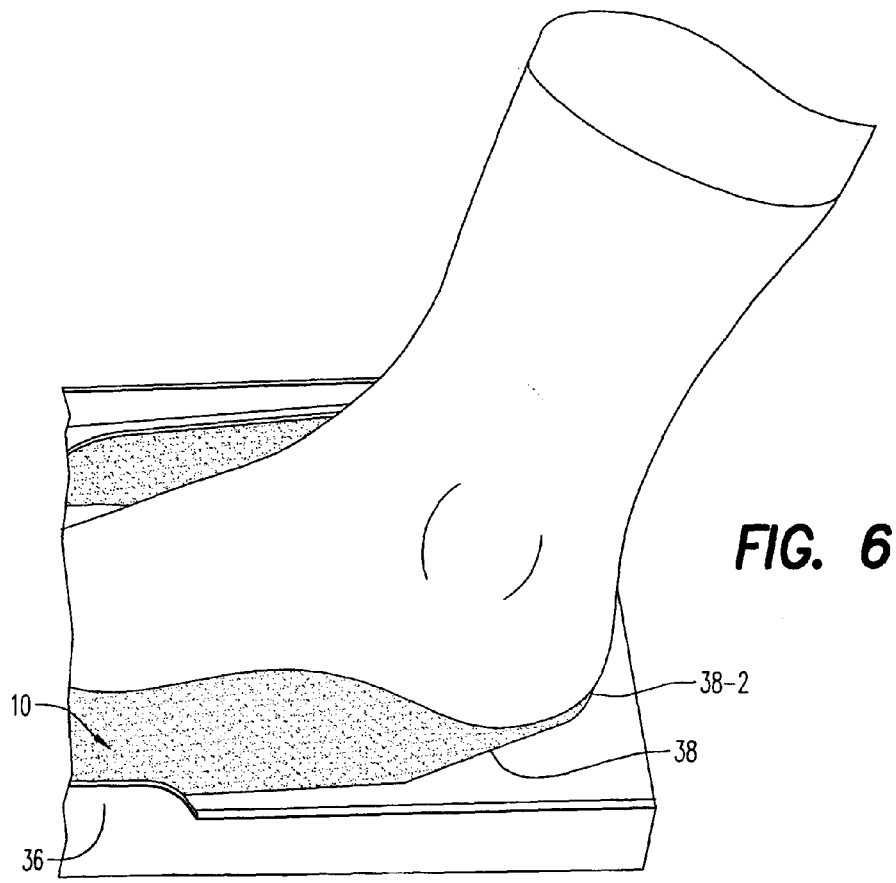
Figure 7:
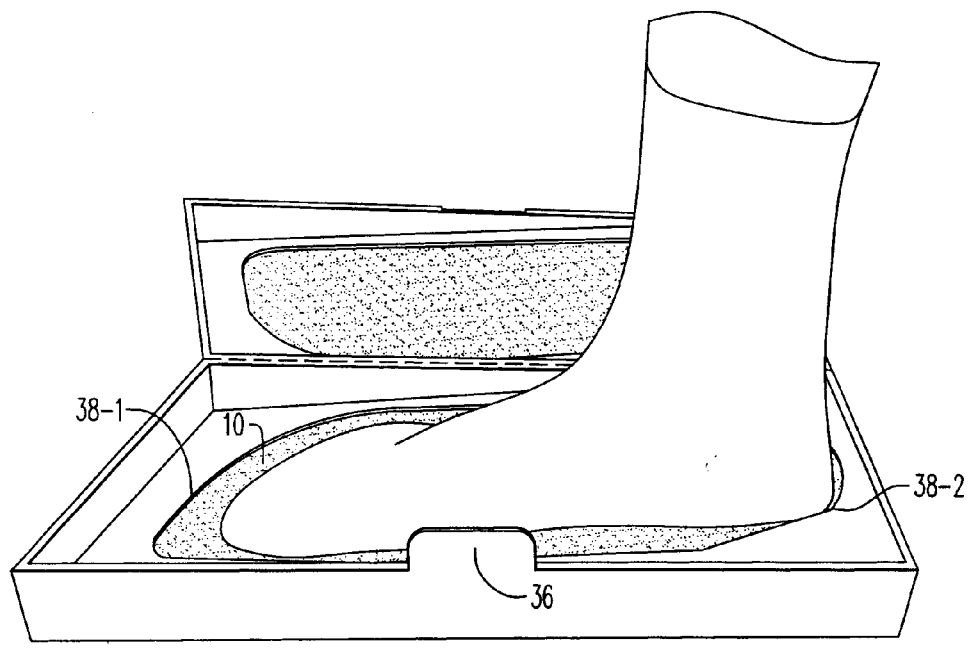
Figure 8:
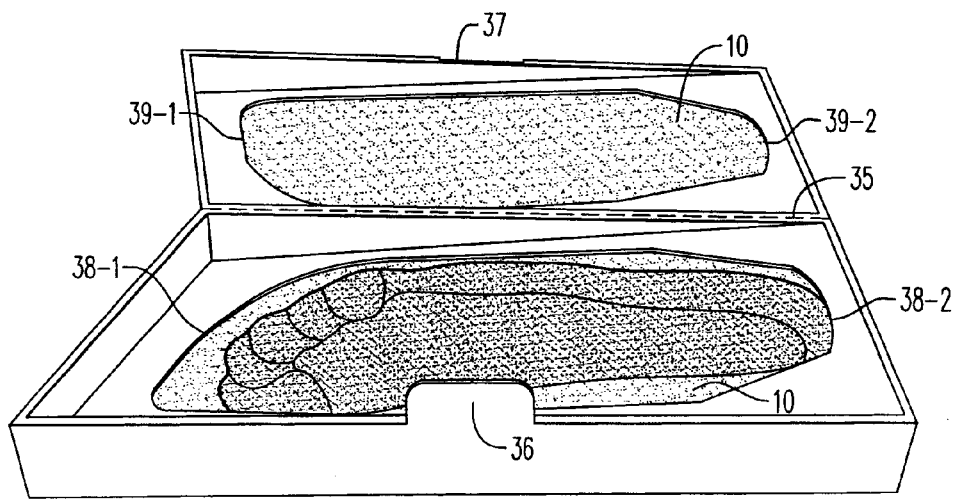
Figure 9:
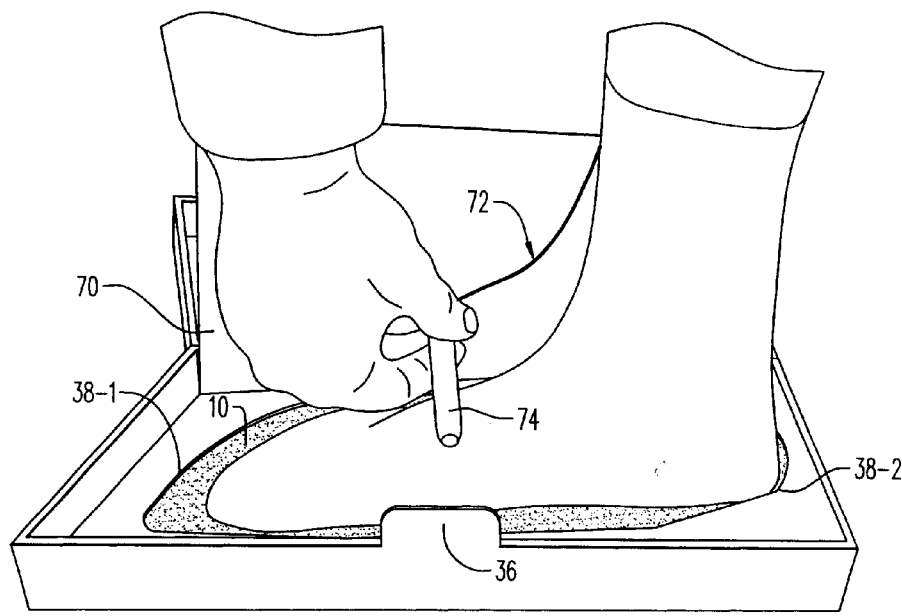
Figure 10:
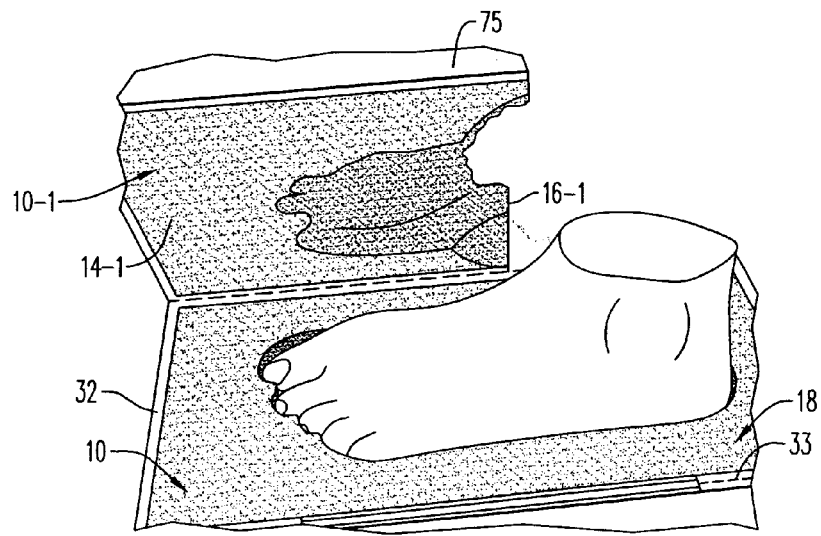
Figure 11:
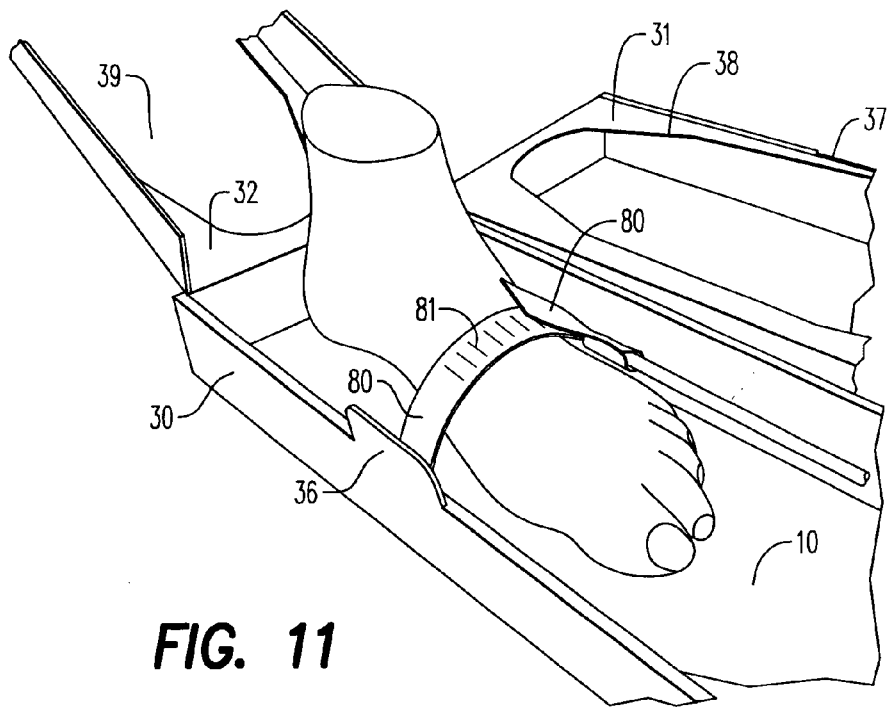
Figure 12:
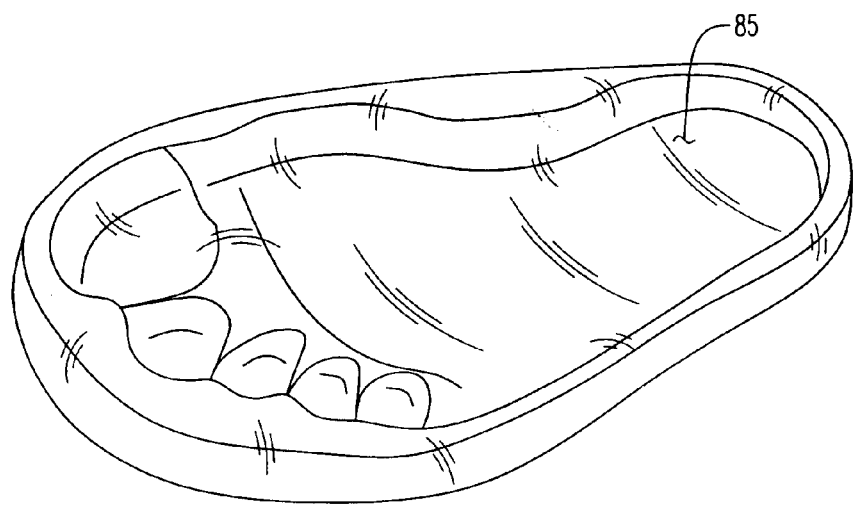

In an alternative embodiment, a thin compliant medium 85, such as, but not limited to, terry cloth or compliant plastic, is placed on the top surface block 10 as shown in FIG. 12. The foot is pressed into compliant medium 85, which in turn compresses block 10. Compliant medium 85 acts to prevent any of block 10 from adhering to the user's foot. In an alternate embodiment, straps 80 are formed on either side of compliant medium 85. In this instance, after pressing one's foot into block 10, the straps are wrapped around the foot and graduations 81 on the strap indicate the height of the instep. This method has the added advantage that if someone fails to press his or her foot all the way into the foam, the perimeter measurement (which indicates the relative instep) will still be correct.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

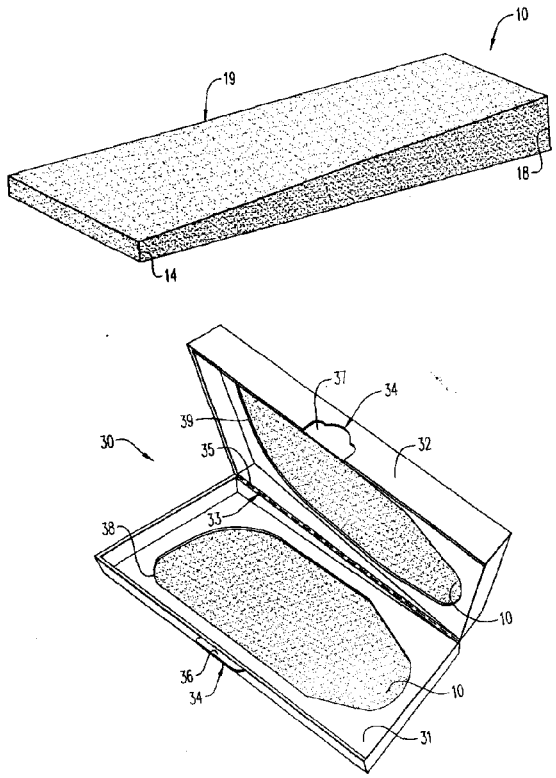

What is claimed is:

1. An apparatus for measuring a person's plantar contour, comprising an impression block formed of a permanently deformable material and having a toe thickness and a heel thickness which is less than the heel thickness; and a first case including said impression block, said case comprising an opening for accessing said impression block wherein said opening, is shaped to approximate the shape of a foot.

2. The apparatus of claim 1, wherein said block is a material selected from the group consisting of expanded phenolic foam and ultra low density expanded polystyrene.

3. The apparatus of claim 1, wherein said heel thickness is in the range from about 20 mm to 35 mm and said toe thickness is in the range from about 10 mm to 15 mm.

4. The apparatus of claim 1, wherein said block includes a compliant medium placed over said block.

5. An apparatus for measuring a person's plantar contour, comprising:
   a first wedge-shaped foam block having a front portion and a back portion wherein said front portion is thinner than said back portion; and
   a first case including said first block, said first case comprising an opening for accessing said first block wherein said opening is shaped to approximate the shape of a foot.

6. The apparatus of claim 5, wherein said first case is formed of a material selected from the group consisting of cardboard and plastic.

7. The apparatus of claim 5, wherein said first case further comprises a first toe portion and a first heel portion and wherein said first block is disposed within said first case such that said front portion is toward said first toe portion and said back portion is toward said first heel portion.

8. The apparatus of claim 7, wherein said heel portion provides a means for aligning the heel of the foot with respect to said opening.

9. The apparatus of claim 7, further comprising a second case which comprises:
   a second toe portion;
   a second heel portion, and
   a second wedge-shaped foam block disposed therein such that a front portion of said second block is toward said second toe portion and a back portion of said second block is toward said second heel portion,
     wherein said opening of said second case is shaped to approximate the shape of the foot opposite the shape of said opening of said first case and said front portion is thinner than said back portion of said second block.

10. The apparatus of claim 9, further comprising hinge means hingedly connecting said first case and said second case for moving the cases between an open position and a closed position.

11. The apparatus of claim 10, wherein said first and second blocks are protected by said first and second cases, respectively, when in said closed position and said first and second blocks are accessible via said openings when in said open position.

12. The apparatus of claim 10, wherein said hinge means comprises a perforated bend line between said first case and said second case.

13. The apparatus of claim 10, further comprising clasp means disposed on said first and second cases for removably sealing said first and second cases in said closed position.

14. The apparatus of claim 13, wherein said clasp means comprises a tab on one of said first and second cases and a matching slot on the other of said first and second cases.

15. The apparatus of claim 9, wherein said opening in said first case is shaped to approximate the shape of a left foot, said opening in said second case is shaped to approximate the shape of a right foot, and said hinge means connects said first case and said second case such that when said openings are presented to the user, said first case is to the right of said second case.

16. An apparatus for measuring a person's plantar contour and instep, comprising:
   a first impression block having a toe thickness and a heel thickness wherein said toe thickness is less than said heel thickness;
   a first case having said first block disposed therein, said first case including an opening for accessing said first block wherein said opening is shaped to approximate the shape of a first foot; and
   at least one strap having graduations associated with said first case and adapted to wrap around the instep of the first foot.

17. The apparatus of claim 16, further comprising a compliant medium placed over said first block.

18. The apparatus of claim 16, wherein said first case further comprises a toe portion and a heel portion and said first block is disposed within said first case such that said toe thickness is toward said toe portion and said heel thickness is toward said heel portion.

19. The apparatus of claim 18, further comprising a second case which comprises:
   a second toe portion;
   a second heel portion,
   a second wedge-shaped foam block disposed therein such that a front portion of said second block is toward said second toe portion and a back portion of said second block is toward said second heel portion, and
   at least one strap having graduations thereon associated with said second case and adapted to wrap around the instep of the second foot,
      wherein said opening of said second case is shaped to approximate the shape of the foot opposite the shape of said opening of said first case and said front portion is thinner than said back portion of said second block.

20. The apparatus of claim 19, further comprising connecting means movably connecting said first case and said second case for moving the cases between an open position and a closed position, wherein said first and second blocks are protected by said first and second cases, respectively, when in said closed position and said first and second blocks are accessible via their respective openings when in said open position.

21. The apparatus of claim 20, further comprising locking means disposed on said first and second cases for removably locking the cases in the closed position.

22. The apparatus of claim 18, wherein the first foot is a left foot, the second foot is a right foot, and said connecting means connects said first case and said second case such that when said openings are presented to the user, said first case is to the right of said second case.

23. A method for measuring a person's plantar contour, comprising:
   placing the plantar contour of the person's foot over a first impression block formed of a permanently deformable material and having a toe thickness such that the toes of the foot are over said toe thickness and the heel of the foot is over said heel thickness; and
   pressing the plantar contour of the foot into said first block to deform said fist block.

24. The method of claim 23, wherein said first block is a material selected from the group consisting of expanded phenolic foam and ultra low density expanded polystyrene.

25. The method of claim 24, wherein said heel thickness is in the range from about 20 mm to 35 mm and said toe thickness is in the range from about 10 mm to 15 mm.

26. The method of claim 23, wherein said first block further comprises a compliant medium over said first block.

27. A method for measuring a person's plantar contour, comprising:
   placing the plantar contour of the person's first foot over a first impression block formed of a permanently deformable material and disposed within a first case wherein, sad first block comprises a toe thickness and a heel thickness wherein said toe thickness is less than said heel thickness, and wherein said first case comprises an opening for accessing said first block wherein said opening is shaped to approximate the shape of the first foot;
   aligning the first foot such that the toes are over said toe thickness and the heel is over said heel thickness; and
   pressing the plantar contour through said opening and into said first block to deform the first block.

28. The method of claim 27, comprising the further step of removing the first foot from said first block.

29. The method of claim 28, comprising
   placing the plantar contour of the person's second foot over a second impression block disposed within a second case wherein, said second block comprises a toe thickness and a heel thickness wherein said toe thickness is less than said heel thickness, and wherein said second case comprises an opening for accessing said second block wherein said opening of said second case is shaped to approximate the shape of the second foot;
   aligning the second foot such that the toes are over said toe thickness and the heel is over said heel thickness; and
   pressing the plantar contour through the opening and into the second block to deform the second block.

30. The method of claim 29, comprising the further step of removing the second foot from said second block.

31. The method of claim 30, further comprising hinge means movably connecting said first case and said second case for moving said first and second cases between an open position and a closed position wherein said first and second blocks are protected by said first and second cases, respectively, when in said closed position and said first and second blocks are accessible via their respective openings when said first and second cases are in said open position, the method comprising:
   moving said first and second cases to said open position before placing the plantar contour of the person's first foot over said first block, and
   moving said first and second cases to said closed position after removing the person's second foot from said second block.

32. The method of claim 31, further comprising clasp means disposed on said first and second cases for removably securing the cases in said closed position, the method comprising:
   unsecuring said clasp means prior to moving said first and second cases to said open position, and
   sealing said clasp means after moving said first and second cases to said closed position.

33. A method for measuring a person's plantar contour and instep, comprising:
   placing the plantar contour of the person's foot over an impression block disposed within a case wherein, said block comprises a toe thickness and a heel thickness, and at least one strap having graduations thereon and associated with said case, and wherein said toe thickness is less than said heel thickness, said case includes an opening for accessing said block, and said opening is shaped to approximate the shape of the foot, aligning the foot such that the toes are over said toe thickness and the heel is over said heel thickness;

pressing the plantar contour through said opening and into said block to deform said block;

wrapping said at least one strap around the instep of the foot; and noting the measurement indicated by said graduations.

34. A method for making a custom insole, comprising:

measuring the plantar contour of a foot by placing the plantar contour over an impression block formed of a permanently deformable material and disposed within a case wherein said block comprises a toe thickness and a heel thickness, said case comprises an opening for accessing said block wherein said opening is shaped to approximate the shape of the foot;

aligning the foot such that the toes are over said toe thickness and the heel is over said heel thickness;

pressing the plantar contour through said opening into said block to deform said block creating an impression therein;

removing the foot from said block;

scanning said impression to create a digitized plantar contour;

providing said digitized plantar contour to a computer controlled milling machining; and directing said computer controlled milling machine to manufacture said custom insole using said digitized plantar contour.

* * * * *

UNITED STATES PATENT AND TRADEMARK OFFICE
CERTIFICATE OF CORRECTION

PATENT NO. : 6,430,831 B1
DATED : August 13, 2002
INVENTOR(S) : Arjen Sundman

It is certified that error appears in the above-identified patent and that said Letters Patent is hereby corrected as shown below:

Delete the title page and substitute therefor the attached title page.

Delete Drawing Sheets 1-12 and substitute therefore the attached Drawing Sheets 1-6.

Signed and Sealed this

Twenty-ninth Day of April, 2003

JAMES E. ROGAN
*Director of the United States Patent and Trademark Office*

United States Patent
Sundman

(12) 
(10) Patent No.: US 6,430,831 B1
(45) Date of Patent: Aug. 13, 2002

(54) METHOD AND APPARATUS FOR MEASURING FOOT GEOMETRY

(75) Inventor: Arjen Sundman, Santa Cruz, CA (US)

(73) Assignee: Amfit, Inc., Santa Clara, CA (US)

(*) Notice: Subject to any disclaimer, the term of this patent is extended or adjusted under 35 U.S.C. 154(b) by 82 days.

(21) Appl. No.: 09/705,106

(22) Filed: Nov. 2, 2000

Related U.S. Application Data

(60) Provisional application No. 60/164,090, filed on Nov. 6, 1999.

(51) Int. Cl.[7] ................................................. A61B 5/103
(52) U.S. Cl. ........................................ 33/515; 33/514.2
(58) Field of Search ................................ 33/515, 1 BB, 33/512, 514.2; 12/1 G, 21

(56) References Cited

U.S. PATENT DOCUMENTS

| | | | |
|---|---|---|---|
| 2,330,317 A | 9/1943 | Stewart | 33/515 |
| 2,472,754 A | 6/1949 | Mead | 33/515 |
| 4,998,354 A | 3/1991 | Silverman et al. | 33/514.2 |
| 5,390,680 A | 2/1995 | Brenner | 33/515 |

*Primary Examiner*—Christopher W. Fulton
(74) *Attorney, Agent, or Firm*—Ohlandt, Greeley, Ruggiero & Perle, L.L.P.

(57) ABSTRACT

An apparatus for measuring a person's plantar contour having a foam impression block with a toe thickness and a heel thickness wherein the toe thickness is less than the heel thickness. A method for measuring a person's plantar contour using such a foam impression block by placing the plantar contour of the person's foot over the foam impression block such that the toes are over the toe thickness and the heel is over the heel thickness; and then pressing the plantar contour into the block to deform the block.

34 Claims, 12 Drawing Sheets